(12) United States Patent
Ando et al.

(10) Patent No.: US 8,937,714 B2
(45) Date of Patent: Jan. 20, 2015

(54) INSPECTING APPARATUS AND INSPECTING METHOD

(75) Inventors: Kimiaki Ando, Hamura (JP); Hiroshi Kikuchi, Hitachi (JP); Yuji Inoue, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 183 days.

(21) Appl. No.: 13/520,460

(22) PCT Filed: Dec. 8, 2010

(86) PCT No.: PCT/JP2010/007127
§ 371 (c)(1),
(2), (4) Date: Jul. 3, 2012

(87) PCT Pub. No.: WO2011/083532
PCT Pub. Date: Jul. 14, 2011

(65) Prior Publication Data
US 2012/0314211 A1 Dec. 13, 2012

(30) Foreign Application Priority Data
Jan. 7, 2010 (JP) .................................. 2010-001703

(51) Int. Cl.
*G01N 21/00* (2006.01)
*G01N 21/95* (2006.01)
(Continued)

(52) U.S. Cl.
CPC ............ *G01N 21/9501* (2013.01); *G01N 21/47* (2013.01); *G01N 21/94* (2013.01); *H01L 22/12* (2013.01)
USPC .................. 356/237.2; 356/237.3; 356/237.6; 356/364

(58) Field of Classification Search
CPC .............. G01N 21/9501; G01N 21/94; G01N 21/8806; G01N 21/956; G01N 21/95607
USPC ............................................ 356/237.2–237.6
See application file for complete search history.

(56) References Cited

U.S. PATENT DOCUMENTS

2004/0252295 A1 12/2004 Miyakawa et al.
2008/0291436 A1* 11/2008 Aiko et al. ................. 356/237.2
(Continued)

FOREIGN PATENT DOCUMENTS

JP 63-315937 12/1988
JP 2004-101438 4/2004
(Continued)

OTHER PUBLICATIONS

International Search Report from International Application No. PCT/JP2010/007127 mailed Mar. 22, 2011.

*Primary Examiner* — Tarifur Chowdhury
*Assistant Examiner* — Isiaka Akanbi
(74) *Attorney, Agent, or Firm* — Brundidge & Stanger, P.C.

(57) ABSTRACT

Provided is a method wherein a multi-anode detector is used for the purpose of detecting scattered light from a wafer, data obtained from the detector (multi-anode) for detecting defects is used, the shape of a beam radiated to the wafer, a rotational shift between the radius direction and the beam long side, and the like are calculated, and the optical axis of the irradiation beam is adjusted. Furthermore, the method is provided with a technique which feeds back the correction quantities for rotation and amplitude to inspection signal data, on the basis of the correction data, and corrects inspection data. Since fine correction with the adjustment of an optics system and signal processing is made possible, positional accuracy of defect inspection and accuracy of defect level (defect size) are improved.

8 Claims, 13 Drawing Sheets

(51) Int. Cl.
  *G01N 21/47* (2006.01)
  *G01N 21/94* (2006.01)
  *H01L 21/66* (2006.01)

(56) References Cited

U.S. PATENT DOCUMENTS

| | | |
|---|---|---|
| 2009/0195775 A1 | 8/2009 | Nakao et al. |
| 2009/0257058 A1* | 10/2009 | Urano et al. ............ 356/364 |
| 2009/0279081 A1 | 11/2009 | Urano et al. |
| 2009/0323051 A1* | 12/2009 | Matsui ................ 356/237.3 |

FOREIGN PATENT DOCUMENTS

| | | |
|---|---|---|
| JP | 2005-003447 | 1/2005 |
| JP | 2007-240512 | 9/2007 |
| JP | 2008-76283 | 4/2008 |
| JP | 2008-96395 | 4/2008 |
| JP | 200896395 | 4/2008 |
| JP | 2009-150725 | 7/2009 |
| JP | 2009-180691 | 8/2009 |
| JP | 2009-236791 | 10/2009 |
| JP | 2009236791 | 10/2009 |
| JP | 2010-85135 | 4/2010 |
| JP | 2010-123700 | 6/2010 |

* cited by examiner

FIG.3
(a)
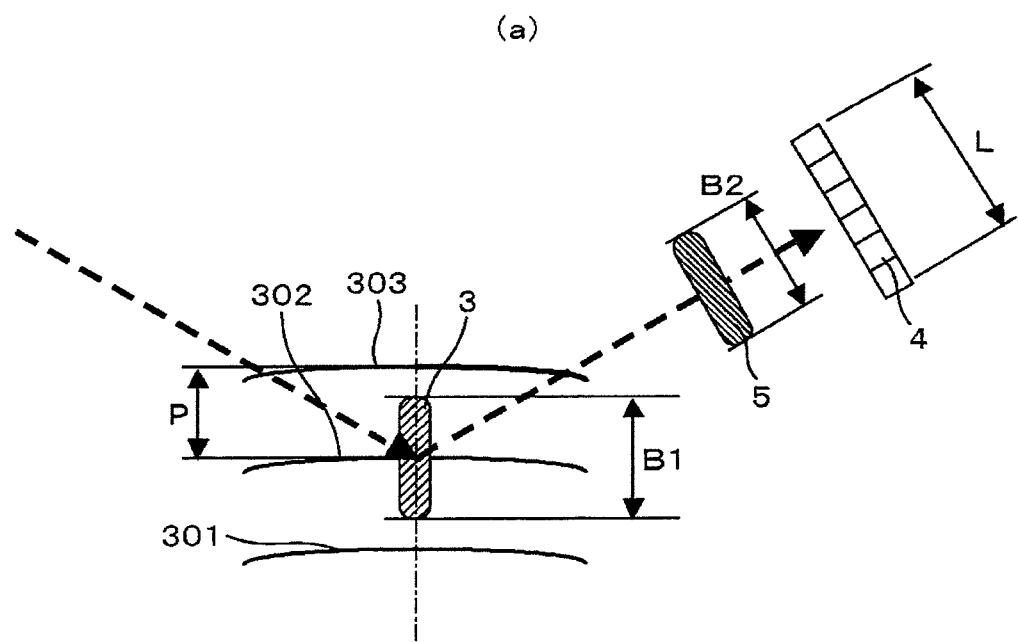
(b)
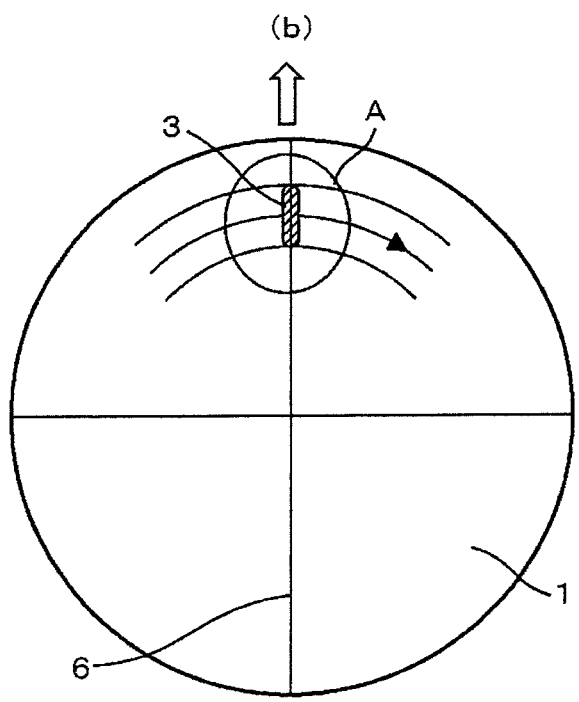

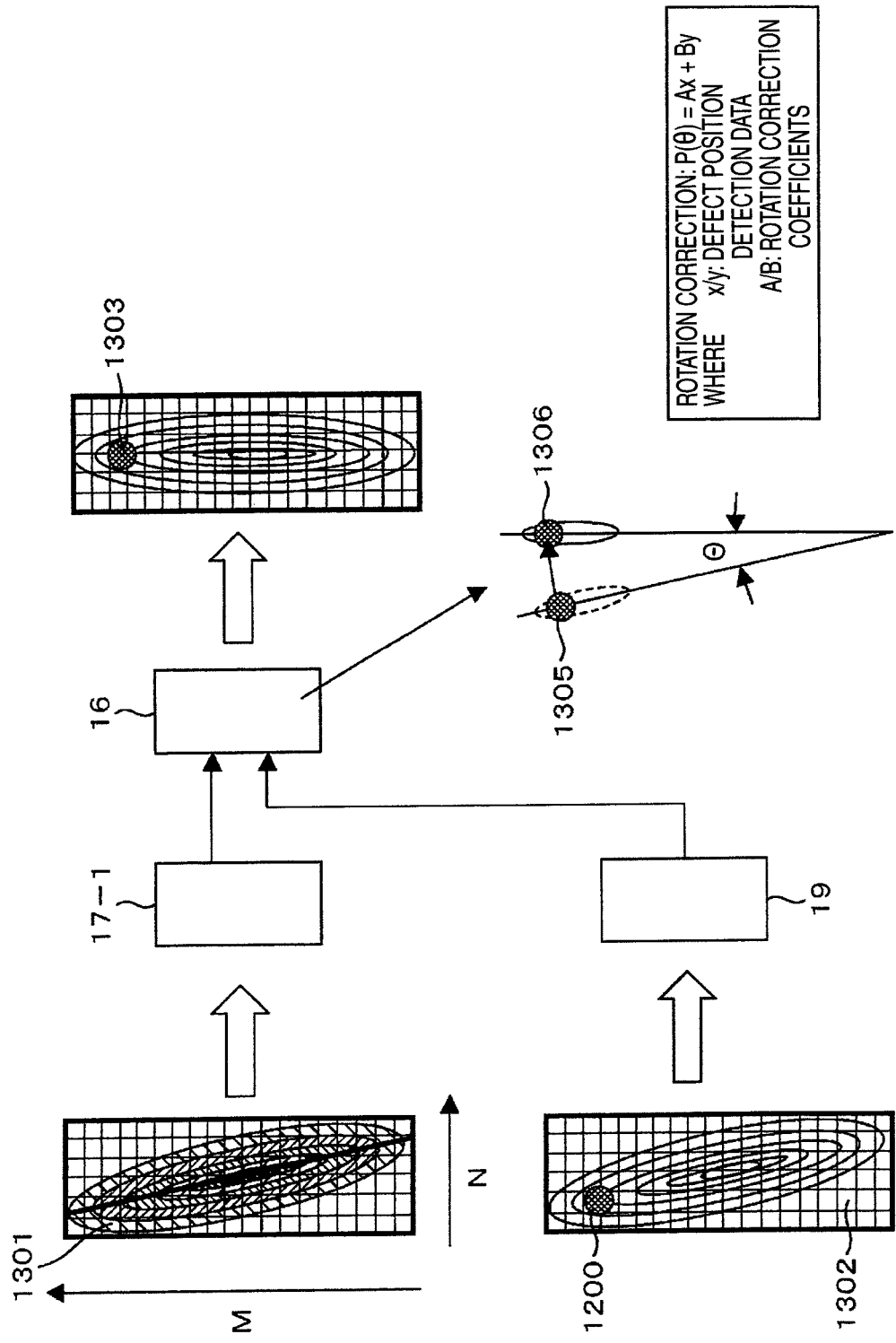

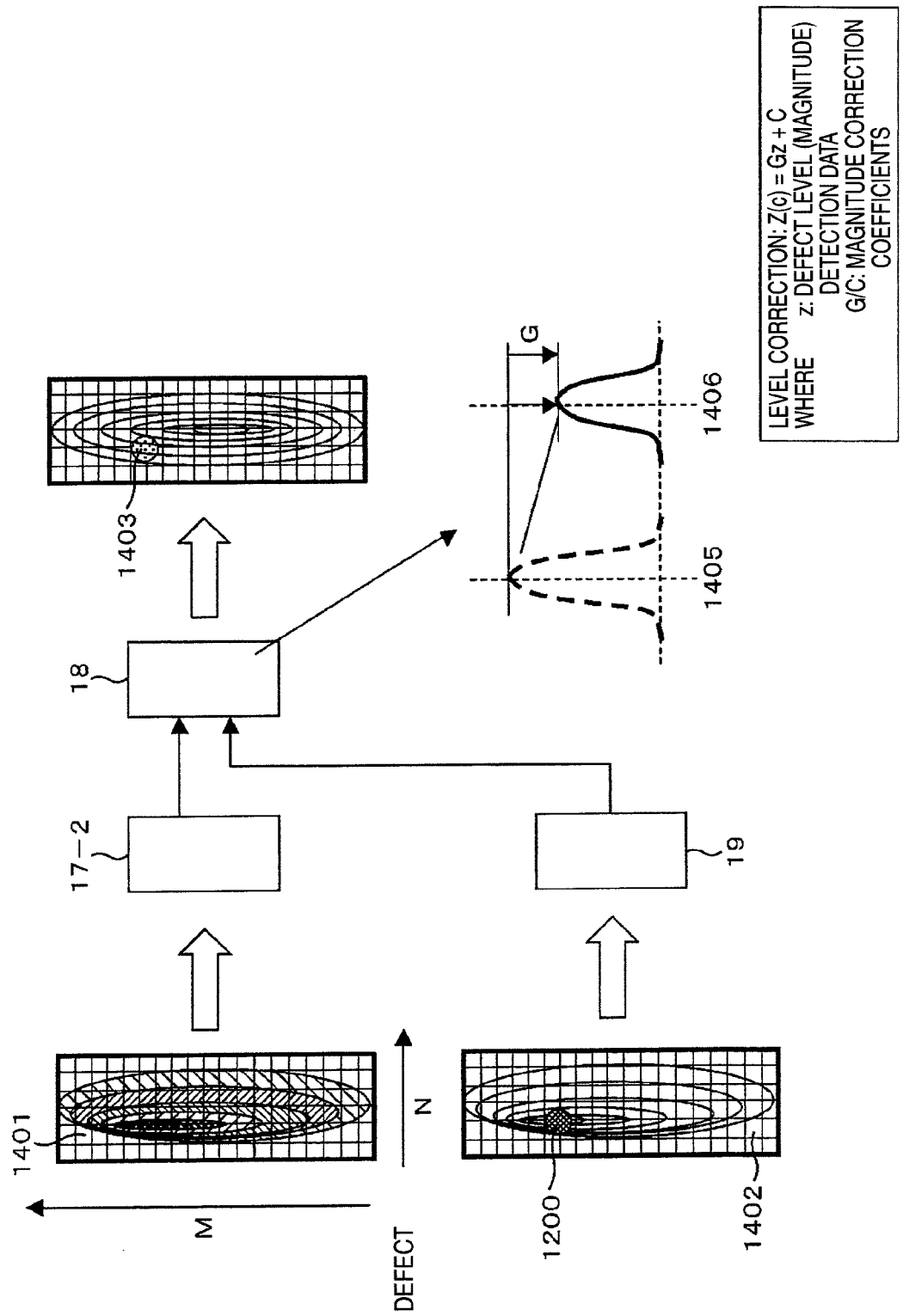

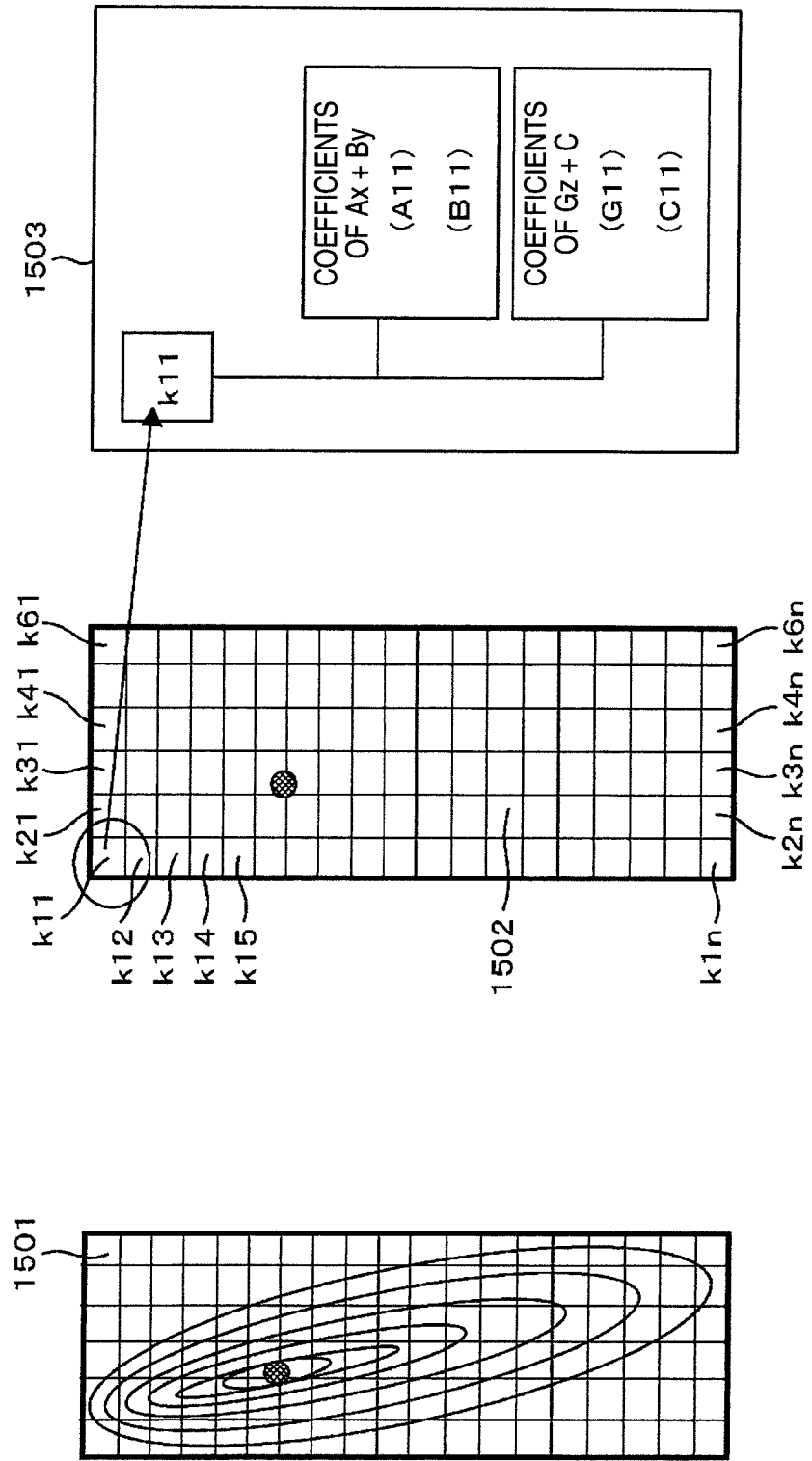

INSPECTING APPARATUS AND INSPECTING METHOD

TECHNICAL FIELD

The present invention relates to a substrate inspecting apparatus and, in particular to an apparatus for inspecting wafers.

BACKGROUND ART

As for semiconductor wafer inspecting apparatuses, there are two kinds: an inspecting apparatus which inspects a wafer while rotating the wafer and an inspecting method while scanning a wafer in the X and Y directions. A method according to the present invention relates to a method for optically irradiating a wafer with a beam while rotating the wafer and moving the wafer rectilinearly in a radial direction, and detecting a defect on the wafer such as a foreign object by utilizing scattered light reflected on the wafer.

As a method for detecting intensity of scattered light of the wafer, using a signal which is output from an angle detector (encoder) attached to a rotational stage, the detection signal is subject to A/D conversion and subsequent signal processing such as filtering to detect a size and coordinates of a foreign object or a defect.

In a foreign-object/defect inspecting apparatus which inspects a surface by rotating a wafer to scan a beam spirally, an elliptical beam which is oblong in the radial direction as for a shape of the beam to be casted with is used.

In a conventional technique, scattered light of the elliptical shape is detected by a single photodetector (for example, a photomultiplier) to detect a foreign object or a defect on a wafer. There is also an example in which a photodetector of the multi-anode type is used instead of a photomultiplier as a method of scattered light detection; however, it becomes necessary to calibrate the optics system with high accuracy such that it is necessary to align the optical axis of the elliptical beam with the multi-anode direction.

As a conventional example concerning a detecting method using a multi-anode, there is an optical inspecting apparatus described in Patent Literature 1 (JP-A-2005-3447). According to Patent Literature 1, it is described that a multi-anode detector is arranged in a long side direction of a beam of an elliptic shape.

CITATION LIST

Patent Literature

Patent Literature 1: JP-A-2005-3447

SUMMARY OF INVENTION

Technical Problem

In an inspecting apparatus for detecting defects by rotating a wafer and using a light beam of an elliptic shape having a long side in the radial direction, it is necessary to align an optical axis of the light beam with an axis in the radial direction. Conventionally, an optical image detection unit for observing the optical axis is disposed separately from a scattered light detection unit to be used for inspection, and the optical axis detection is conducted using the optical image detection unit whereas defect detection is conducted using the scattered light detection unit. Not taken into consideration is the point that, when two separate detectors are used in this way, even if the optical axis is adjusted in the optical image detection unit, the optical axis is not necessarily in alignment in the scattered light detection unit and the accuracy of the position of the defect detection is not improved.

The present invention provides a method for using a multi-anode detector as a scattered light detecting method and aligning an optical axis of an elliptical beam with a light receiving axis of a one-dimensional sensor of a multi-anode.

Solution to Problem

A first feature of the present invention is to have an irradiation optics system which irradiates a wafer with first light of an elliptical shape, a multi-anode detection system which detects second light from the wafer, and an adjustment unit which adjusts an optical axis of the first light using a detection result of the multi-anode detecting system.

A second feature of the present invention is to have a correction unit which corrects the detection result using the detection result of the multi-anode detection system.

A third feature of the present invention is that a length of the first light from the irradiation optics system in its long side direction is longer than a scanning pitch of a transfer system and a length of detection elements of the multi-anode detection system is longer than a length of the second light from a substrate in its long side direction.

A fourth feature of the present invention is that the correction unit conducts rotation correction or amplitude correction of the first light.

A fifth feature of the present invention is that an intensity distribution of the first light is a Gaussian distribution or a distribution which is constant in the radial direction or the θ direction.

Advantageous Effects of Invention

According to the present invention, it is possible to improve the accuracy of defect detection.

BRIEF DESCRIPTION OF DRAWINGS

FIG. 3 is a diagram showing a relation between a feed pitch of a wafer and a beam shape;

FIG. 13 is a diagram showing a method for conducting rotation correction of foreign object/defect information;

FIG. 14 is a diagram showing a method for conducting amplitude correction of foreign object/defect information; and FIG. 15 is a diagram showing relations between two-dimensional input data and correction coefficients.

DESCRIPTION OF EMBODIMENTS

Hereafter, embodiments of the present invention are described with reference to the drawings.

First, a configuration example of a semiconductor wafer foreign object/defect detecting apparatus is described.

Figure 12:
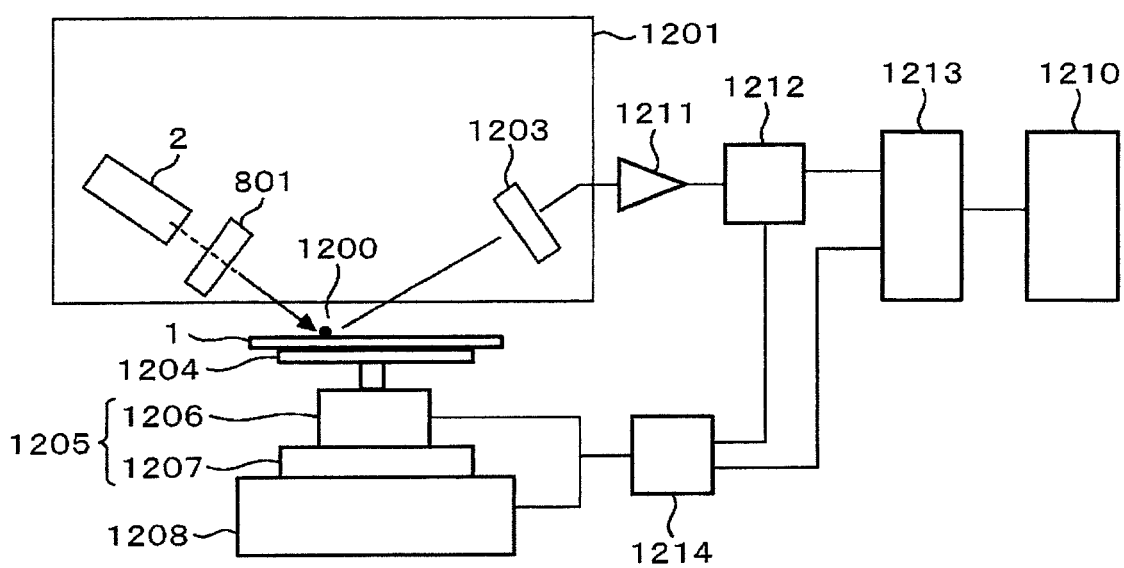
FIG. 12 is a diagram showing an overall configuration of a foreign object/defect inspecting apparatus according to the present invention.

FIG. 12 is a diagram showing an overall configuration of a foreign object/defect inspecting apparatus using a foreign object/defect inspecting method according to the present invention. A semiconductor wafer 1, which is an object to be inspected, is vacuum-adsorbed to a chuck 1204 and the chuck 1204 is mounted on a moving stage for the to-be-inspected object 1205, composed of a rotating stage 1206 and a translating stage 1207, and a Z stage 1208. An illuminating/detecting optics system 1201 arranged above the semiconductor wafer 1 is an optics system for illumination and detection. A laser light source is used as a light source 2 of illumination light, an irradiation beam exiting from the light source 2 passes through an irradiation lens 801 to form a beam of an elliptical shape which is oblong in a direction of a radius r, the wafer 1 is irradiated with it, and light scattered upon hitting a foreign object or a defect 1200 is detected by a photodetector 1203 and input to an amplifying circuit 1211 after being converted to an electric signal.

The moving stage for the to-be-inspected object 1205 causes an illumination spot relatively scan in spiral on the whole surface of the semiconductor wafer 1 by changing a rotating movement θ which is a primary scanning and a translating movement R which is an auxiliary scanning in combination with time.

While the rotating stage makes one revolution, the auxiliary scanning moves by Δr. In the present embodiment, scanning of the illumination spot is conducted from an inner circumference toward an outer circumference of the semiconductor wafer 1; however, it may be conducted in reverse. Furthermore, in the present embodiment, the rotating stage 1206 is driven with an approximately constant angular velocity and the translating stage 1207 is driven with an approximately constant linear velocity over the whole area from an inner circumference to an outer circumference of the semiconductor wafer 1. As a result, the relative linear velocity of movement of the illumination spot with respect to the surface of the semiconductor wafer 1 becomes faster on an outer circumference compared with on an inner circumference. To detect the coordinate position of the primary scanning θ and the coordinate position of the auxiliary scanning r during inspection, an inspection coordinate detecting mechanism 1214 is attached to the moving stage for the to-be-inspected object 1205. In the present embodiment, a rotary encoder of the optical reading type is used to detect the coordinate position of the primary scanning θ and a linear encoder of the optical reading type is used to detect the coordinate position of the auxiliary scanning r; those using other detection principles may also be used as long as they are sensors capable of detecting an angle or a position on a straight line with high accuracy.

An output of the amplifying circuit 1211 is converted to a digital signal by an A/D converter circuit 1212; a defect size and a defect position are calculated by a defect detection circuit 1213 using coordinate data of r and θ which are output from the inspection coordinate detecting mechanism 1214, and output to a controller 1210.

In this configuration, a foreign object or a defect 1200 passes the illumination spot and a scattered light signal is obtained from the photodetector 1203. In the present embodiment, a photomultiplier tube is used as the photodetector 1203; a photodetector according to another detection principle may be applicable as long as it is a photodetector which can detect scattered light from a foreign object with high sensitivity.

Figure 1:
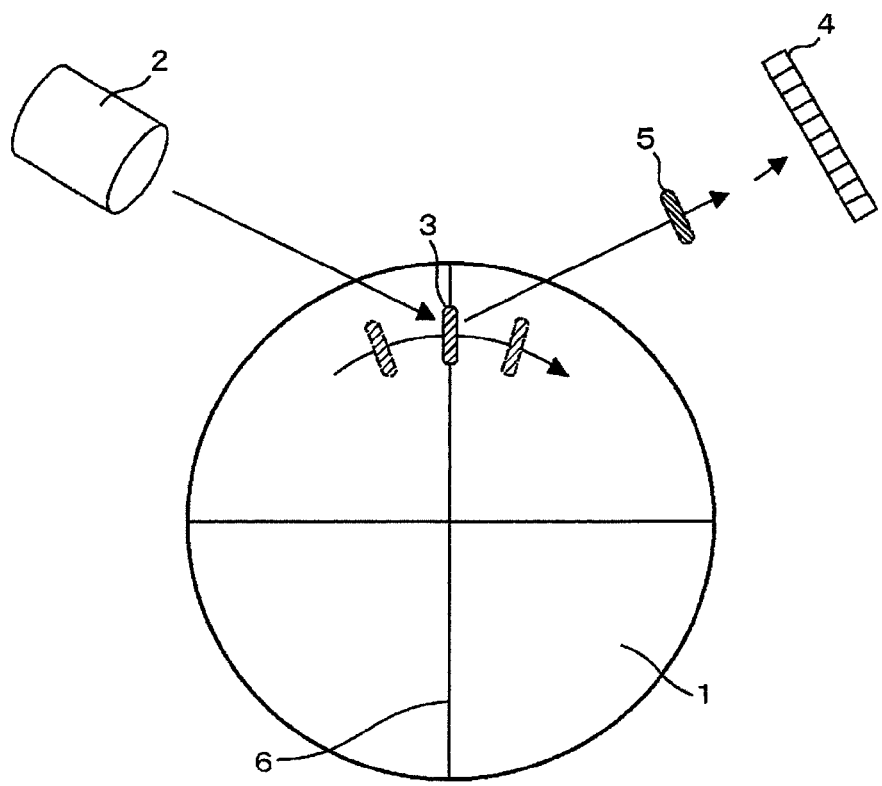
FIG. 1 is a diagram showing a configuration of a defect detecting method according to the present invention.

FIG. 1 is a diagram showing a configuration of a defect detecting method according to the present invention.

By a light beam of the light source 2 being casted onto the wafer 1 with a shape of an irradiation light beam 3 and hitting a radial pattern 6, a scattered light beam shape 5 is generated and is input to a multi-photodetector 4.

The multi-photodetector 4 is a one-dimensional photodetector having a plurality of detecting elements arranged in a radial direction.

As the irradiation light beam 3, a light beam of an elliptical shape having a long side in the radial direction of the wafer is used. The casted irradiation light beam 3 generates the scattered light beam shape 5 when it hits a foreign object or a defect (unevenness on the wafer). When there is radial unevenness or a radial pattern, scattered light becomes a signal projecting a shape of an irradiation beam. When a beam is shone onto a radial pattern, therefore, the multi-photodetector detects beam intensity in the radial direction.

Figure 2:
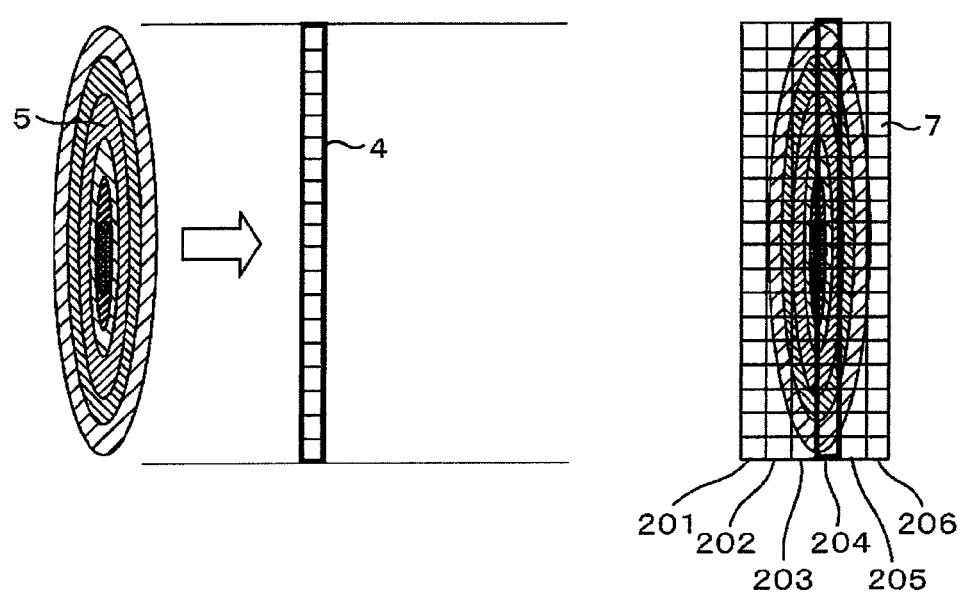
FIG. 2 is a diagram showing a relation between scattered light and a multi-photodetector.

FIG. 2 is a diagram showing a relation between scattered light and the multi-photodetector.

The scattered light beam shape 5 scattered upon hitting a radial pattern on the wafer is an elliptical shape as shown in FIG. 2 and a signal of beam intensities as represented by contour lines is obtained.

In the multi-photodetector 4, elements are arranged along the long side direction of the light beam and it can obtain data 204 corresponding to one column in a longitudinal direction of a beam intensity distribution 7. By rotating the wafer, the irradiation beam is rendered to scan on the radial pattern in a lateral direction in the present figure; by fetching data obtained from the multi-photodetector at constant time intervals, converting to digital signals, and storing in a memory or the like, a two-dimensional intensity distribution signal consisting of signals of data 201 to data 206 shown in the beam intensity distribution 7 is obtained. A length of the irradiation beam in the long side direction is equivalent to a scanning pitch with which light scans the wafer in spiral and a size of the elliptical beam in the short side is approximately in the range of 10 to several tens of μm. For example, in order to take in a beam having a width of 10 μm at constant intervals and obtain a two-dimensional intensity distribution signal, sampling is conducted to acquire data so that 10 μm is divided approximately into five to ten sections.

FIG. 3 is a diagram showing a relation between a feed pitch of the wafer and a beam shape.

In the apparatus which conducts defect inspection while rotating the wafer, the wafer is moved with a constant feed pitch while casting the irradiation light beam 3 to the wafer 1 to perform inspection in spiral. Part (a) of FIG. 3 is an enlarged view of Part A which is irradiated with the light beam. Reference numerals 301 to 303 denote tracks which the laser beam has passed (or is going to pass) when the wafer is moved with a constant feed pitch. The feed pitch of the wafer, namely, the scanning pitch of light becomes P. Furthermore, denoting the length of the casted light beam in the long side direction by B1, there is a relation of B1>P. Moreover, denoting a length of scattered light in the long side direction by B2 and a length of arrangement of the detecting elements in the multi-photodetector by L, it is configured to satisfy a relation of L>B2. By doing so, it is possible to optically receive and convert signals of the elliptical light beam in the long side direction with the multi-photodetector 4 at once.

Figure 4:
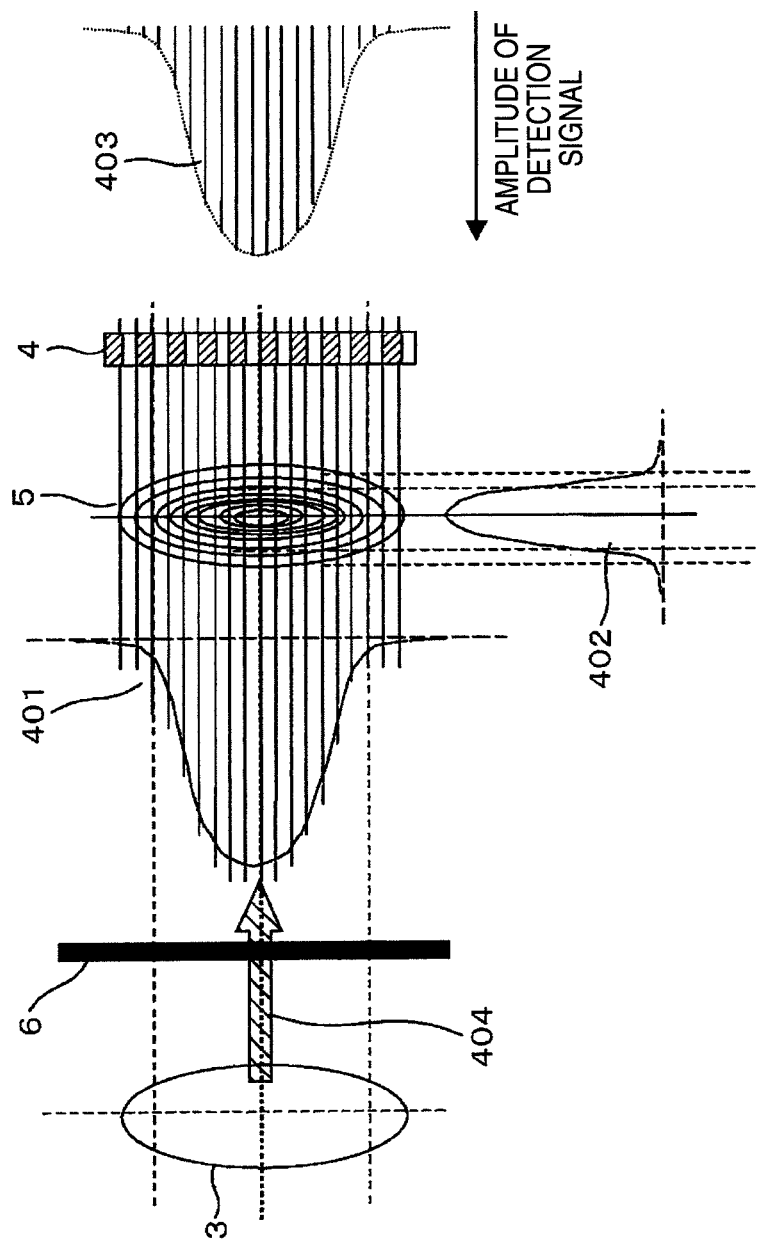
FIG. 4 is a diagram showing signal intensities of light received by the multi-photodetector.

FIG. 4 is a diagram showing signal intensities of light received by the multi-photodetector.

The irradiation light beam 3 scans over the radial pattern 6 on the wafer in a direction of an arrow 404 so that the scattered light beam shape 5 is obtained with the multi-photodetector 4.

The intensity of the irradiation light typically takes a shape of a Gaussian distribution and an R-direction waveform of the scattered light beam intensity in the long side direction (the vertical direction in FIG. 4 or the radial direction on the wafer) of the beam of the elliptical shape becomes one as represented by a reference numeral 401. Further, a signal waveform in the short side direction (the horizontal direction in FIG. 4 or the circumference (θ) direction on the wafer) becomes one shown by a reference numeral 402. As output signals of the multi-photodetector 4, output signals from respective detectors are obtained as shown as an output signal 403.

Figure 5:
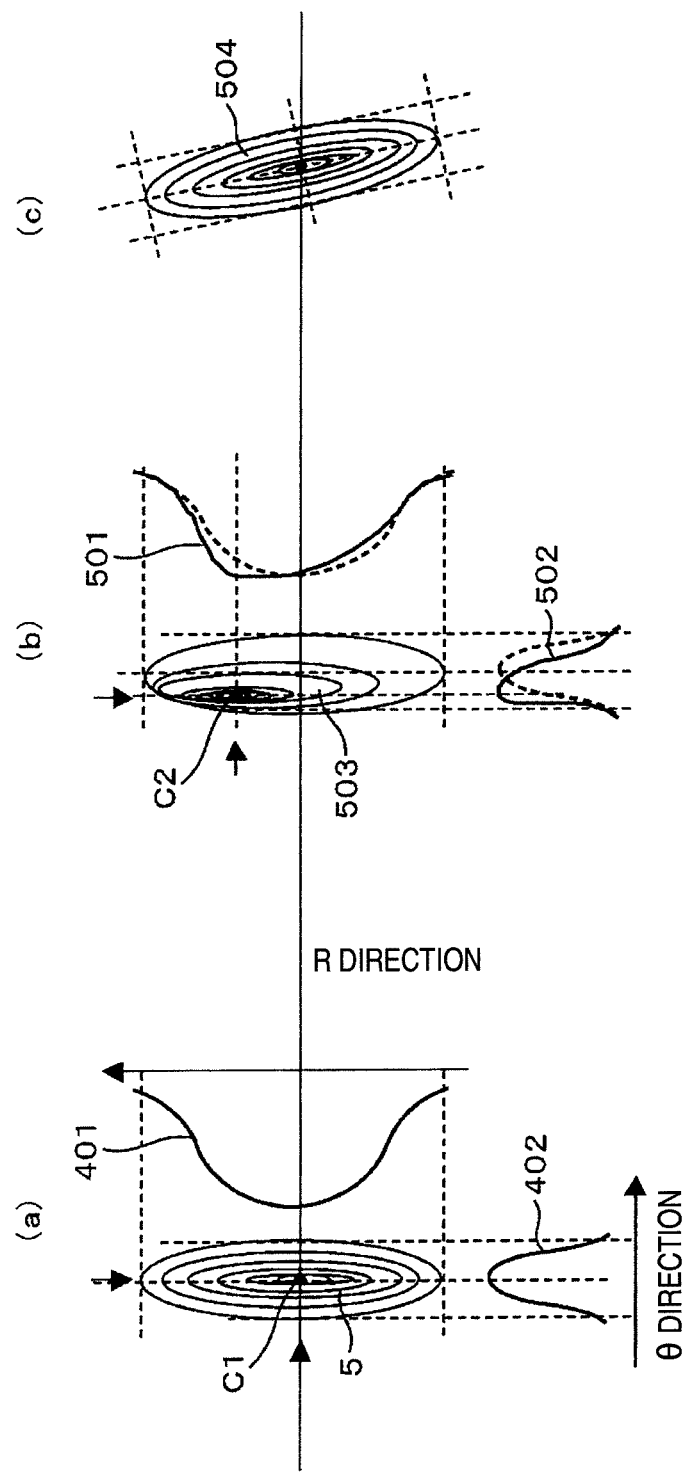
FIG. 5 is a diagram showing examples of an irradiation light beam.

FIG. 5 is a diagram showing examples of the irradiation light beam.

Part (a) of FIG. 5 is a diagram in a case where scattered light with irradiation light having a nice Gaussian distribution is received in the same way as FIG. 4; a center of the beam intensity is located at a beam center C1, and both the R-direction waveform 401 and the θ-direction output 402 form undistorted Gaussian distribution waveforms. Part (b) of FIG. 5 and Part (c) of FIG. 5 show examples of cases where the light intensity distribution is distorted. Part (b) of FIG. 5 shows an example in which the center C2 of the light beam intensity is not the center of the elliptical beam; each of the R-direction output 501 and the θ-direction output 502 is not a Gaussian distribution but has a distorted shape. When the irradiation light beam is distorted, then the scattered light is similarly distorted and a position of the maximum value of a defect signal is shifted. If the light distribution is distorted as in FIG. 5(b), even though there is a foreign object in the center position C1 of the beam in itself, the maximum value of the detection signal is in a position of C2 when a position and a size of the foreign object on the wafer is detected and, consequently, it would be falsely detected as if the position of the foreign object were located near C2. Further, Part (c) of FIG. 5 shows a waveform in a case where the irradiation light beam has inclination with respect to the radial direction. In a case where the light beam is tilted in this way as well, the position of the detection result of the foreign object is detected with a shift in the rotation direction or the like so that it causes deterioration of accuracy of the detection position.

Figure 6:
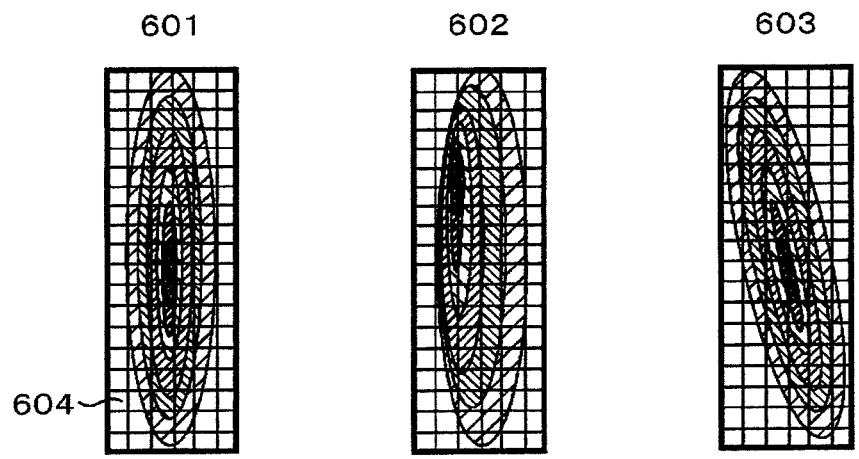
FIG. 6 shows examples in cases where a two-dimensional image is generated from signals detected by the multi-photodetector.

FIG. 6 shows examples in cases where a two-dimensional image is generated from signals detected by the multi-photodetector. A two-dimensional image 604 is a signal which is made as a two-dimensional image by arranging several data of signals detected from the multi-photodetector in the θ direction. A scattered light intensity two-dimensional image 601 is an image corresponding to the photo-detection signal shown in Part (a) of FIG. 5. A scattered light intensity two-dimensional image 602 corresponds to the photo-detection signal shown in Part (b) of FIG. 5 and it is an image in which the maximum value of the signal intensity is shifted from the center of the beam. Further, a scattered light intensity two-dimensional image 603 corresponds to the photo-detection signal shown in Part (c) of FIG. 5, and it is an image in which the light beam is rotated.

In the present invention, examples having light intensities of Gaussian distributions have been described; in many of irradiation beams used for defect detection, there are cases where a beam having a constant (flat) light intensity in the radial direction and the θ direction is used besides a beam of a light intensity having a Gaussian distribution.

Figure 7:
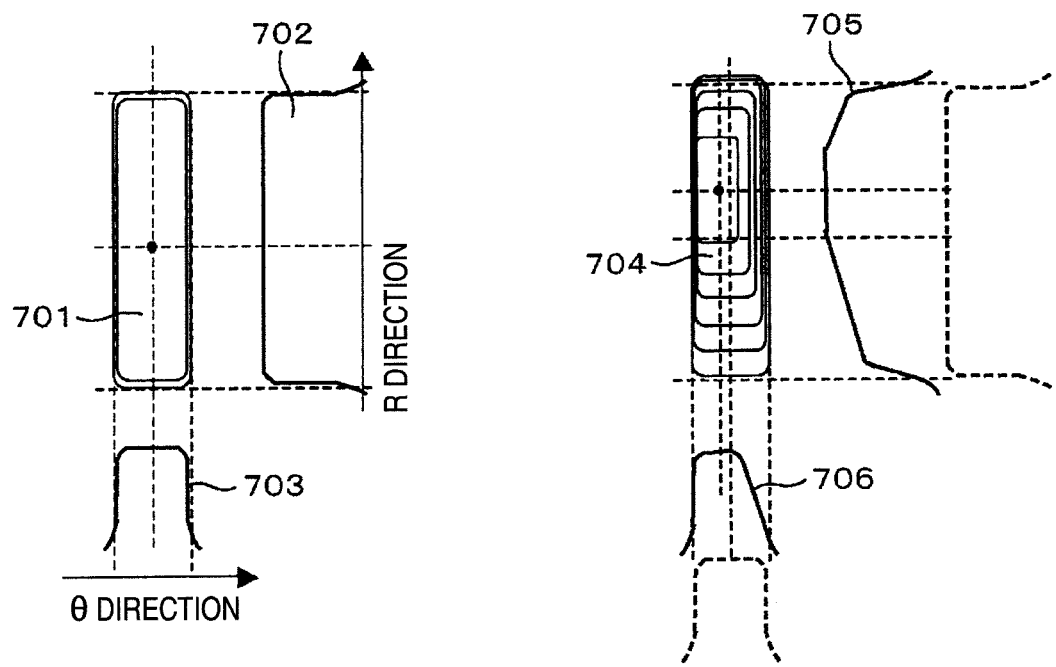
FIG. 7 shows an example of an irradiation beam having a nearly constant light intensity in the radial direction and the θ direction.

FIG. 7 shows an example of an irradiation beam having a nearly constant light intensity in the radial direction and the θ direction.

Part (a) of FIG. 7 shows a detection signal in a case where a beam having a constant normal intensity is casted. As for the beam waveforms of a constant intensity irradiation beam 701, an R (radial) direction waveform 702 and a θ (circumference) direction waveform 703 are obtained. Part (b) of FIG. 7 shows a detection signal in a case where a beam having non-uniform normal intensities is shone. As for the beam waveforms of a non-uniform intensity irradiation beam 704, an R (radial) direction waveform 705 and a θ (circumferential) direction waveform 706 are obtained.

Also in the case where a beam of a constant intensity is used, the beam shape can be measured in this way and it becomes possible to correct the beam intensity or correct the rotation of the irradiation beam.

Figure 8:
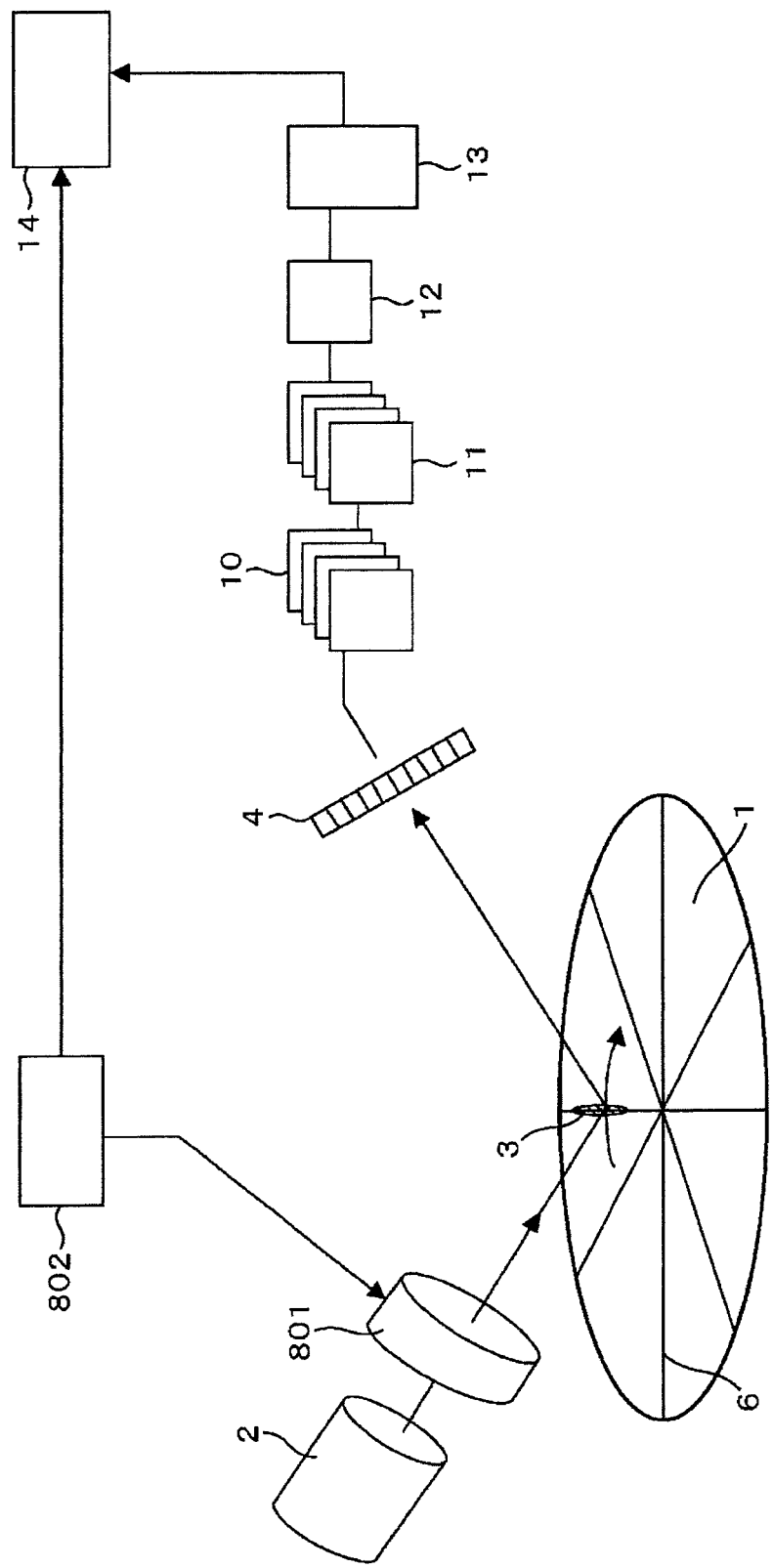
FIG. 8 is a diagram showing a system configuration as a first embodiment of the present invention.

FIG. 8 is a diagram showing a system configuration as a first embodiment of the present invention.

A light beam radiated from a light source 2 passes through an optical axis correction mechanism 801 and is casted on a wafer 1. A radial pattern 6 is engraved on the wafer and scattered light which strikes and is reflected from the radial pattern is converted from optical signals to electric signals at respective elements by a plurality of elements by the multi-photodetector 4. The detection signals converted to the electric signals are amplified by amplifiers 10 disposed for respective elements and convert to digital signals by A/D converters 11 in respective signals. Respective signals obtained from the multi-photodetector are subjected to A/D conversion and, then, input to a memory circuit 12 to be stored in a form of a two-dimensional image. The image input to the memory is subjected to signal processing with a scattered light detection processing circuit 13 and transmitted to a controller 14. In the scattered light detection processing circuit 13, while conducting detection processing for a position of a foreign object or a defect from scattered light, discrimination of sizes of foreign objects and the like are conducted. In addition, in the present invention, intensity distribution information of the beam is calculated in the scattered light detection processing circuit 13 from the two-dimensional image signal and its result is transmitted to the controller 14. The controller 14 finds magnitude of the maximum value of the irradiation beam, position information, and inclination angle information of the scattered light with a radius R taken as reference from information of the scattered light intensity distribution; it further generates data for adjusting an optical axis, controls the optical axis correction mechanism 801 via an optical axis adjustment/control circuit 802, and conducts adjustment so that the irradiation light beam has original intensities of a Gaussian distribution and the long side of the elliptical beam coincides with the radial direction.

Figure 9:
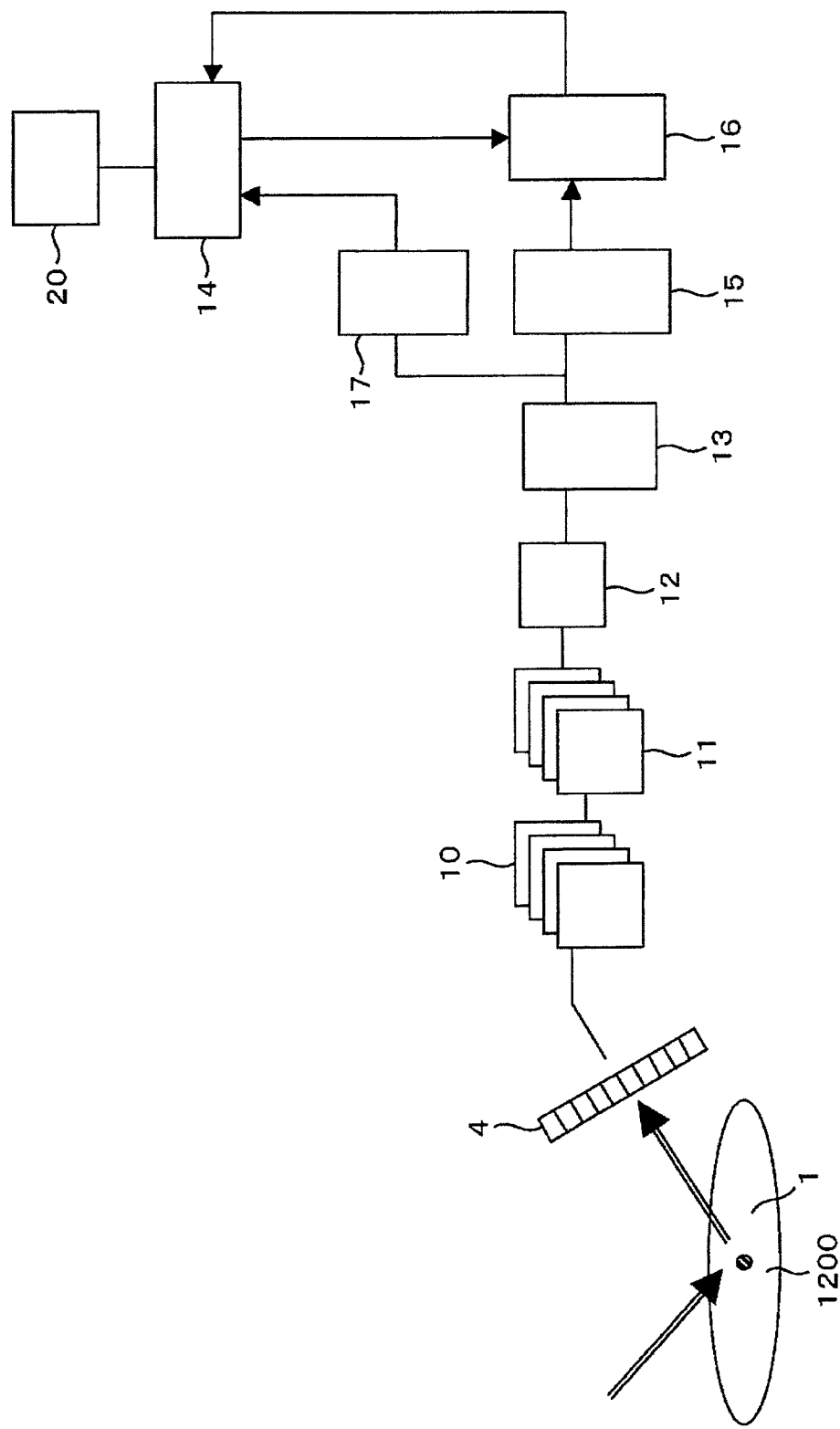
FIG. 9 is a diagram showing a system configuration as a second embodiment of the present invention.

FIG. 9 is a diagram showing a system configuration as a second embodiment of the present invention.

Whereas, in the embodiment shown in FIG. 8, detection of the magnitude of the maximum value of the irradiation beam, the position information, and the inclination angle information of the scattered light with the radius R taken as reference is conducted by the controller 14, in the embodiment shown in FIG. 9, a beam center position coordinate detection circuit 15 and a beam intensity distribution coefficient calculation circuit 17 are provided in a stage subsequent to the scattered light detection processing circuit 13, intensity distribution coefficients are transmitted to the controller 14, correction data for defect detection positions are generated by the controller 14, and correction of the light intensity of scattered light and correction of rotation are conducted by a defect position coordinate correction circuit 16.

In the present embodiment, although a circuit for optical axis correction shown in FIG. 8 is not illustrated, the position of a foreign object or a defect can be detected with high accuracy by using together the optical axis correction mechanism 801 and the defect position coordinate correction circuit 16.

Also, a shape of the light beam and calculated correction data are displayed on a GUI interface 20 based on data transmitted to the controller 14. By displaying the beam shape and the correction data and thereby informing a user of the state of the light beam, adjustment of the optics system is facilitated.

Figure 10:
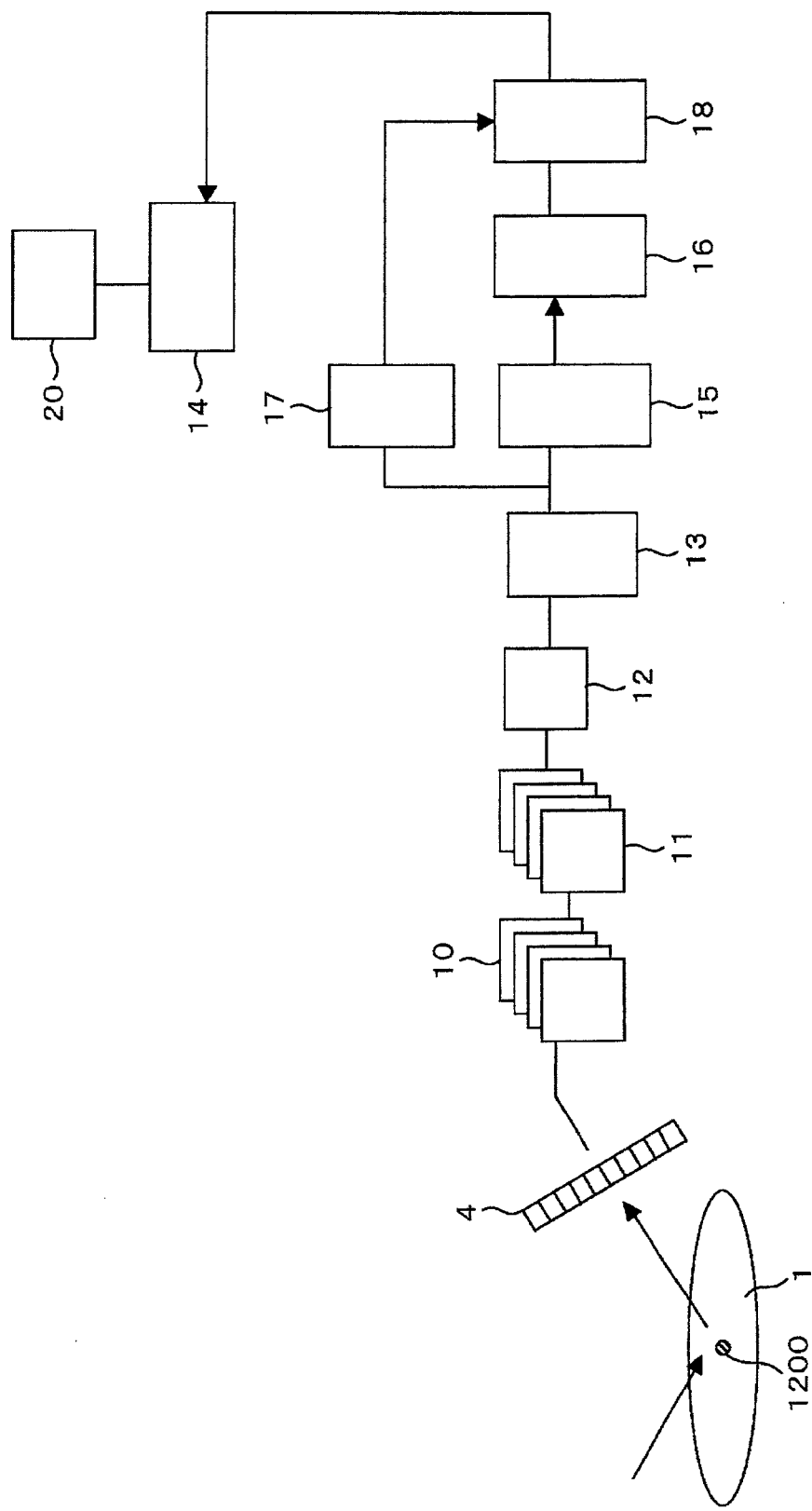
FIG. 10 is a diagram showing a system configuration as a third embodiment of the present invention.

FIG. 10 is a diagram showing a system configuration as a third embodiment of the present invention.

In the present embodiment, a beam intensity correction circuit 18 is provided in a stage subsequent to the defect position coordinate correction circuit 16 to conduct signal amplitude correction especially for distortion of the light beam in the radial direction based on data from the beam intensity distribution coefficient calculation circuit 17. Contents of the defect position coordinate correction circuit 16 and the beam intensity correction circuit 18 are described with reference to FIG. 13 and FIG. 14.

Figure 11:
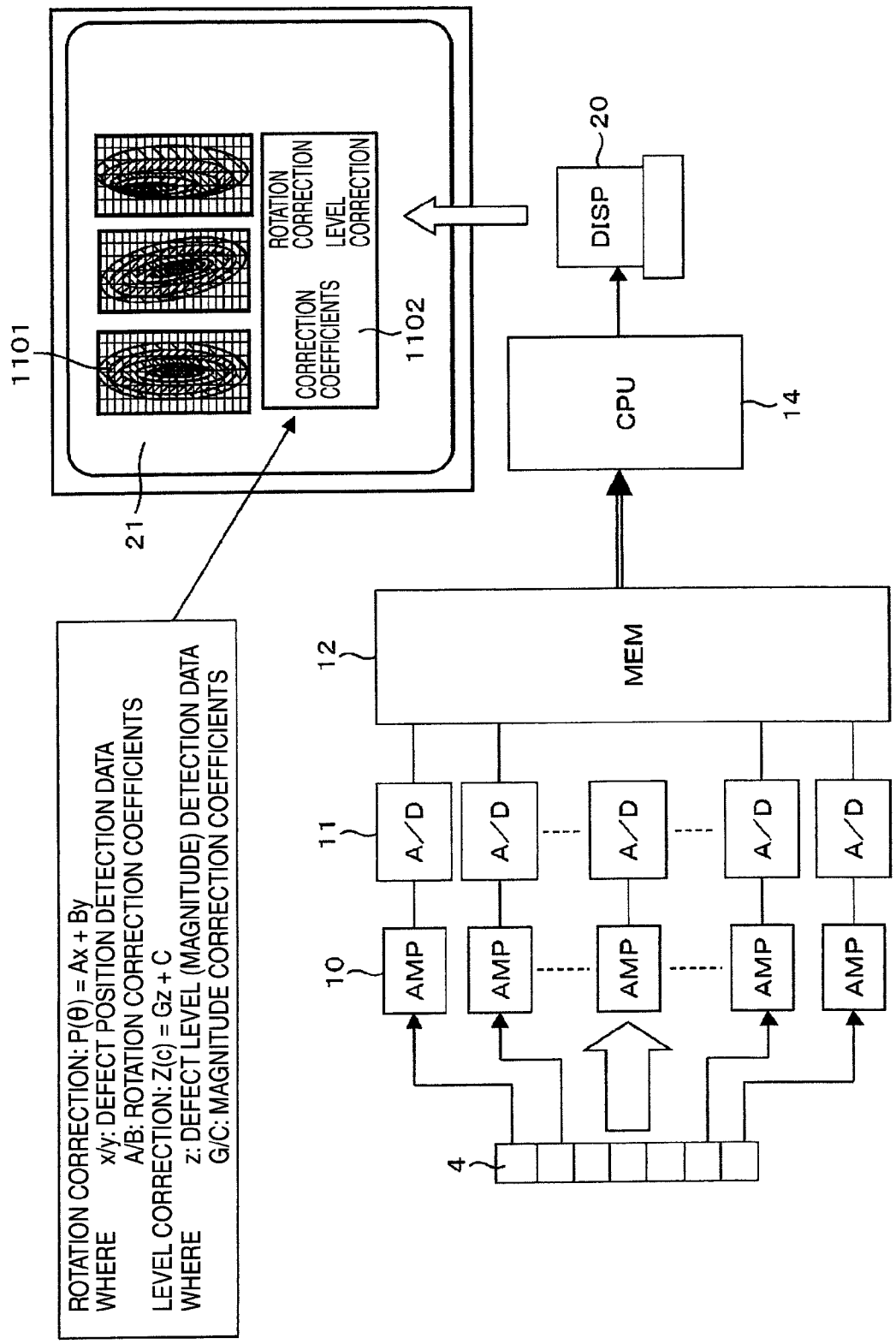
FIG. 11 is a diagram showing relations between a distribution measurement of a light beam and GUI display.

FIG. 11 is a diagram showing relations between a distribution measurement of the light beam and GUI display.

Outputs of the multi-photodetector 4 are converted to digital signals by amplifiers 10 and A/D converters 11 which are disposed for respective detectors and input to a memory circuit 12.

While inputting one-dimensional data of the radial direction scattered from a radial pattern on the wafer, as described earlier, the multiphotodetector 4 stores data of the θ direction centered around the maximum value of the scattered light intensity into the memory circuit 12. Data are stored in the memory as two-dimensional image data as indicated by a reference numeral 1101. The data stored in the memory circuit 12 are transmitted to the controller 14 and the controller 14 displays the light beam shape and the like using the GUI interface (display device) 20.

An example of display on the GUI interface (display device) 20 is shown as a reference numeral 21. On the GUI interface, contour line display 1101 of the intensities corresponding to the intensity distribution of the light beam and display of correction data of the light beam obtained from the intensity distribution data or the like are conducted.

As examples of the correction data of the light beam data, there are rotation correction data and level (amplitude) correction data. An example set of correction equations and correction coefficients is shown below.

Rotation correction of light beam:

$$P(\theta)=Ax+By \quad \text{(Equation 1)}$$

x/y ... XY coordinates of a two-dimensional image
A/B ... correction amounts (correction coefficients) in the X and Y directions Level (amplitude) correction:

$$Z(c)=Gz+C \quad \text{(Equation 2)}$$

z ... an amplitude value at each point of a two-dimensional image
G/C ... a gain correction coefficient and a shift correction amount Rotation correction and amplitude correction of the light beam are conducted by conducting correction calculations at each point of two-dimensional image data using the above-described correction data.

FIG. 15 is a diagram showing relations between two-dimensional input data and correction coefficients. A shift amount of the center position of the light beam, rotation angle data with respect to the radial direction, and the like are calculated using a two-dimensional image 1501 which is input, and a correction coefficient table 1502 is provided as data for correcting them. The correction coefficient table 1502 is a two-dimensional correction coefficient data table (memory) which contains the beam shape, and correction coefficients kij (i=1~6, j=1~n) are stored for respective points. Each correction coefficient has contents as indicated by coefficient data 1503. The coefficient data 1503 indicates, for example, contents of k11, and A11 and B11 are stored as coefficients of the rotation correction (Ax+By) and G11 and C11 are stored as coefficients of the amplitude correction (Gz+C).

Rotation correction and amplitude correction for a detected foreign object or a defect are conducted using the correction coefficients described with reference to FIG. 15.

FIG. 13 is a diagram showing a method for conducting rotation correction of foreign object/defect information.

By a defect position coordinate detection circuit 19 coordinates of a defect 1200 are detected with an input of a defect detection signal 1302. On the other hand, by an intensity distribution coefficient detection circuit 17-1 data (An and Bn shown in FIG. 15) for conducting rotation correction are taken out of beam intensity distribution correction data 1301, coefficients for rotation correction corresponding to foreign object/defect coordinates obtained with the aforementioned defect [position coordinate detection circuit 19 are taken out, and a correction calculation is conducted with the defect position coordinate correction circuit 16. By performing rotation correction with the defect position coordinate correction circuit, a detected defect position 1305 is corrected by an angle θ and position information is corrected to a true defect position 1306 to obtain defect detection data 1303.

FIG. 14 is a diagram showing a method for conducting amplitude correction of foreign object/defect information.

By the defect position coordinate detection circuit 19, coordinates of the defect 1200 are detected with a defect detection signal 1402 as an input. On the other hand, by an intensity distribution coefficient detection circuit 17-2 data Gn and Cn shown in FIG. 15) for conducting amplitude correction are taken out of beam intensity distribution correction data 1401, coefficients for amplitude correction corresponding to foreign object/defect coordinates obtained with the aforementioned defect position coordinate detection circuit 19 are taken out, and a correction calculation is conducted with the beam intensity correction circuit 18. By performing amplitude correction with the beam intensity correction circuit, the magnitude of a detected defect signal 1405 is corrected by a gain G, resulting in correction to a true defect amplitude 1406 to become corrected defect detection data 1403.

Incidentally, the shape of the irradiation beam may not be an elliptical shape but may be the shape of a spot. Furthermore, the configuration of the inspecting apparatus is not limited to that of the present embodiment; the detector may be a sensor having a plurality of pixels such as CCD's, or a scheme of condensing scattered light using an ellipsoid may be used. In addition, the inspection object is not restricted to a wafer, but it may be a hard disk substrate or the like.

Reference Signs List 1 wafer,
2 light source,
3 irradiation light beam,
4 multi-photodetector,
5 scattered light beam shape,
6 radial pattern,
7 beam intensity distribution,
10 amplifier,
11 A/D converter,
12 memory circuit,
13 scattered light detection processing unit,
14 controller,
15 beam center position coordinate detection circuit,
16 defect position coordinate correction circuit,
17 beam intensity distribution coefficient calculation circuit,
18 beam intensity correction circuit,
19 defect position coordinate detection circuit,
20 GUI interface,
21 GUI display example,
401 R-direction waveform,
601, 602 and 603 scattered light intensity two-dimensional image,
701 constant intensity irradiation beam,
801 optical axis correction mechanism,
802 optical axis adjustment/control circuit,
1200 defect,
1203 photodetector,
1205 moving stage for to-be-inspected object,
1208 Z stage.

The invention claimed is:

1. An inspecting apparatus which inspects a substrate, comprising:
 a transfer system which moves a substrate;
 an irradiation optics system which irradiates the substrate with first light of an elliptical shape, a length of the first light in a long side direction on the substrate being longer than a scanning pitch of the transfer system;
 a multi-anode detection system which detects second light from the substrate, a length of detection elements of the multi-anode detection system being longer than a length of the second light in a long side direction on a detection surface of the multi-anode detection system; and
 an adjustment unit which adjusts an optical axis of the first light using a detection result of the multi-anode detection system.

2. The inspecting apparatus according to claim 1, wherein an intensity distribution of the first light is a Gaussian distribution, or a distribution which is constant in a radial direction and a θ direction.

3. The inspecting apparatus according to claim 1, wherein the multi-anode detection system comprises an array of a plurality of elements in a long side direction of the second light.

4. The inspection apparatus according to claim 1, wherein the correction unit obtains inclination angle information of the second light with respect to a radial direction of the substrate based on an intensity distribution of the second light acquired from a detection result of the multi-anode detection system, and adjust an optical axis of the first light so that a long axis direction of the first light coincides with a radial direction of the substrate using the inclination angle information of the second light.

5. An inspecting apparatus which inspects a defect on a substrate, comprising:
 a transfer system which moves a substrate;
 an irradiation optics system which irradiates the substrate with first light of an elliptical shape, a length of the first light in a long side direction on the substrate being longer than a scanning pitch of the transfer system;
 a multi-anode detection system which detects second light from the substrate, a length of detection elements of the multi-anode detection system being longer than a length of the second light in a long side direction on a detection surface of the multi-anode detection system; and
 a correction unit which obtains a center position and an intensity distribution of the second light using a detection result from the multi-anode detection system, and corrects a detection result of the defect based on the center position and the intensity distribution of the second light.

6. The inspecting apparatus according to claim 5, wherein the correction unit conducts rotation correction or amplitude correction of the first light.

7. The inspecting apparatus according to claim 5, wherein an intensity distribution of the first light is a Gaussian distribution, or a distribution which is constant in a radial direction and a θ direction.

8. The inspection apparatus according to claim 5, wherein the multi-anode detection system comprises an array of a plurality of elements in a long side direction of the second light.

* * * * *